United States Patent [19]
Martinez

[11] 4,076,023
[45] Feb. 28, 1978

[54] RESEALABLE DEVICE FOR REPEATED ACCESS TO CONDUIT LUMENS

[75] Inventor: Felix Jesus Martinez, Demarest, N.J.

[73] Assignee: Erika, Inc., Rockleigh, N.J.

[21] Appl. No.: 600,980

[22] Filed: Aug. 1, 1975

[51] Int. Cl.² ............................................. A61M 5/00
[52] U.S. Cl. ................................. 128/214 R; 138/103
[58] Field of Search ............ 128/214 R, 214 C, 214Z, 128/214.4, 247, 275; 138/103, 118, 140, 147

[56] References Cited

U.S. PATENT DOCUMENTS

| | | | |
|---|---|---|---|
| 2,832,338 | 4/1958 | Ryan | 128/214 |
| 3,254,650 | 6/1966 | Collito | 128/334 C |
| 3,327,709 | 6/1967 | Nehring et al. | 128/214 D |
| 3,447,570 | 6/1969 | Collins | 138/151 |
| 3,456,965 | 7/1969 | Gajewski et al. | 128/334 C X |
| 3,734,095 | 5/1973 | Santomieri | 128/214.4 |
| 3,814,137 | 6/1974 | Martinez | 138/103 |
| 3,850,202 | 11/1974 | Morgan | 128/214 R X |
| 3,990,445 | 11/1976 | Lundquist | 128/214 R |

FOREIGN PATENT DOCUMENTS

| | | | |
|---|---|---|---|
| 2,049,513 | 3/1971 | France | 128/214 R |

*Primary Examiner*—Dalton L. Truluck
*Attorney, Agent, or Firm*—Morgan, Finnegan, Pine, Foley & Lee

[57] ABSTRACT

A resealable device for providing repeated access to the lumen of a fluid transmitting conduit including a puncturable elastomeric member maintained in radial compression and limited longitudinal expansion about the conduit to reseal punctures in the elastomeric member and provide a compression seal between the elastomeric member and the conduit. Advantageously, the elastomeric member is held in a state of radial compression and limited longitudinal expansion by a rigid windowed jacket having fixed transverse stops. Moreover, the jacket is formed of a material which is substantially impenetrable to needles or cannulae in normal usage.

6 Claims, 5 Drawing Figures

RESEALABLE DEVICE FOR REPEATED ACCESS TO CONDUIT LUMENS

The present invention relates to resealing devices and more particularly to a resealable device for providing repeated access to conduit lumens.

Generally, in the medical field the fluid flowing through a conduit is sampled, drugs injected, or pressures monitored by inserting a needle or cannula into the lumen of the desired conduit. One approach is to utilize a concentric resilient sleeve, which may or may not be banded at each end, for inserting a needle or cannula therethrough and into the lumen or bore of the conduit. This approach is less than satisfactory in at least two respects: Firstly, the resulting openings in the conduit are not hermetically sealed with the resulting danger that air may be aspirated and fluid, e.g., blood, may leak through the puncture site. With repeated injections there is a substantial likelihood of leakage. Secondly, if, as often occurs, the person making the injection exerts too great a force on the conduit the needle will pass through the opposite side of the tube and into the person's finger, resulting in a nasty puncture which may lead to hepatitis or other infectious diseases.

Another approach is to utilize a second concentric sleeve for applying radial compression to the inner sleeve. Although this approach has provided some improvement in resealing punctures, it is less than satisfactory in providing a hermetic seal over the range of pressures encountered, both positive and negative, in normal extracorporeal circuits. Further, this approach does not protect the user from nasty punctures and is not satisfactory for multiple puncture usage.

It is an object of the present invention to provide a resealable device for repeated access to conduit lumens.

It is a still further object of the present invention to provide a resealable device for repeated access to conduit lumens which automatically hermetically reseals itself after each puncture.

It is a still further object of the present invention to provide a resealable device for repeated access to conduit lumens which protects a user against accidental puncture which may result in hepatitis or other infectious diseases.

Briefly, the resealable device according to the present invention includes a puncturable elastomeric member having a predetermined thickness and length concentrically arranged about a conduit and rigid compression means concentrically arranged about the elastomeric member for radially compressing and longitudinally expanding the elastomeric member; the compression means exposes a portion of the elastomeric member for access by needles and cannulae and includes fixed transverse stops for limiting the longitudinal expansion of the elastomeric member to concentrate and maintain the elastic recoil energy of the elastomeric member against the conduit enabling the elastomeric member to reseal punctures therein and also seal punctures in the conduit, thereby preventing leakage from the conduit lumen after access thereto.

The preferred embodiment of the present invention is shown in the drawings which should be construed as only illustrative of the features of the present invention; it should be expressly understood that the invention should not be construed as being limited solely to the preferred embodiment. A description of the preferred embodiment follows, in which.

Figure 1:
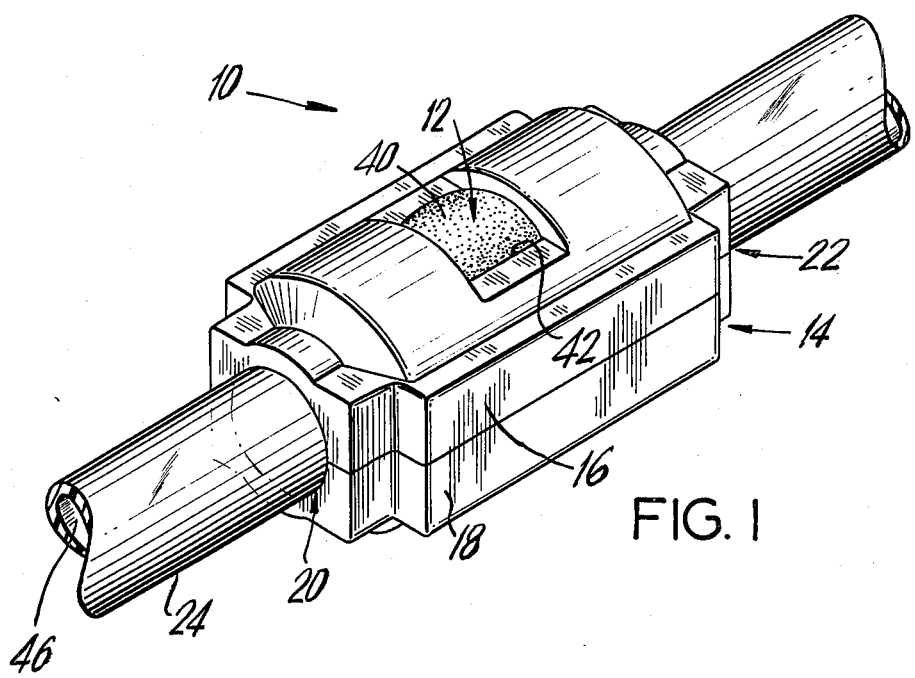
FIG. 1 is a perspective view of the resealable device for repeated access to conduit lumens.

Referring to FIG. 1, the resealable device for repeated access to conduit lumens is generally illustrated at 10. The resealable device 10 includes a puncturable elastomeric member or tube 12, e.g., formed of latex, and a rigid jacket 14 for compressively housing the elastomeric tube 12 therein. The jacket 14 is preferably formed from a pair of mating plastic elements 16 and 18 which are fixedly assembled about the elastomeric member 12, e.g., by ultrasonic welding. When employing ultrasonic welding, an energy director in the form of a peripheral rib 19 is formed on one of the elements 16 or 18, as shown the rib 19 is on element 16 in FIG. 2, and the elements 16 and 18 are ultrasonically welded about the elastomeric tube 12. The assembled elements 16 and 18 include reduced diameter portions 20 and 22, see also FIG. 4, for receiving a fluid transmitting conduit or tube 24, e.g., of polyvinyl chloride or other readily puncturable material. The elastomeric tube 12 is concentrically mounted about the fluid transmitting tube 24 and the jacket 14 is arranged concentrically mounted about the elastomeric tube 12.

Figure 2:
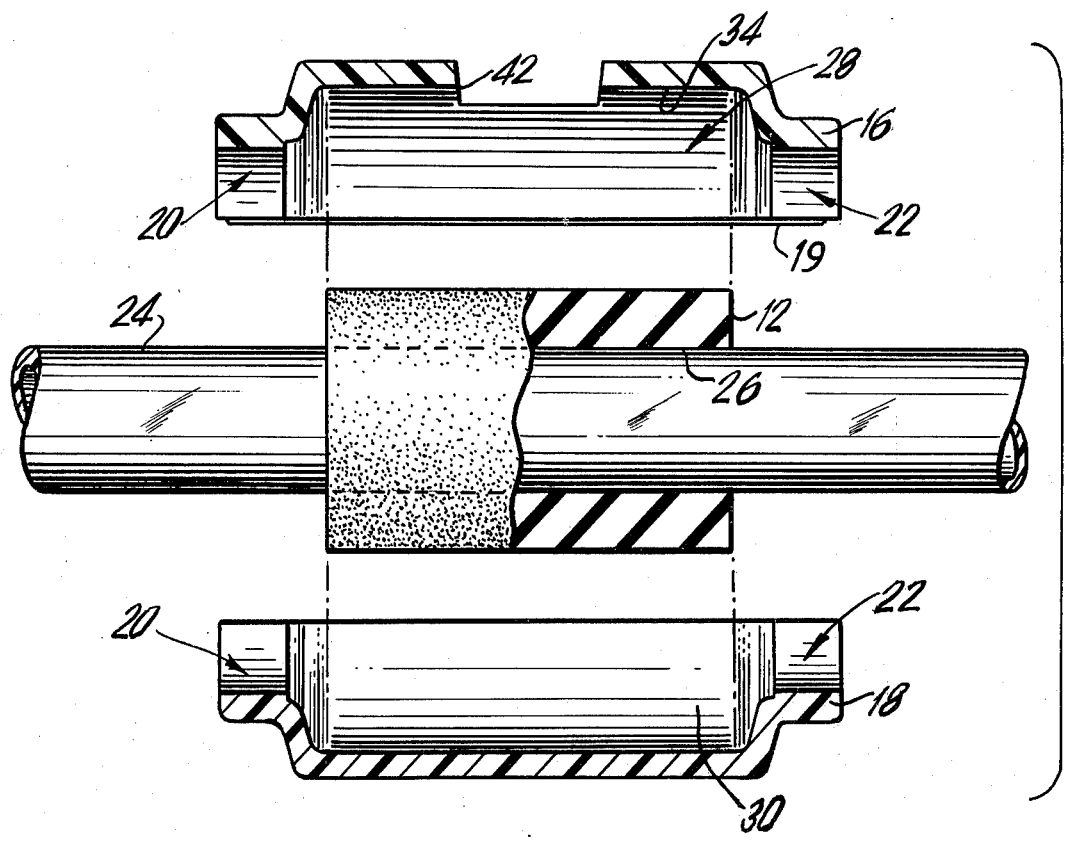
FIG. 2 is an exploded elevational view in partial section of the resealable device of FIG. 1.
Figure 3:
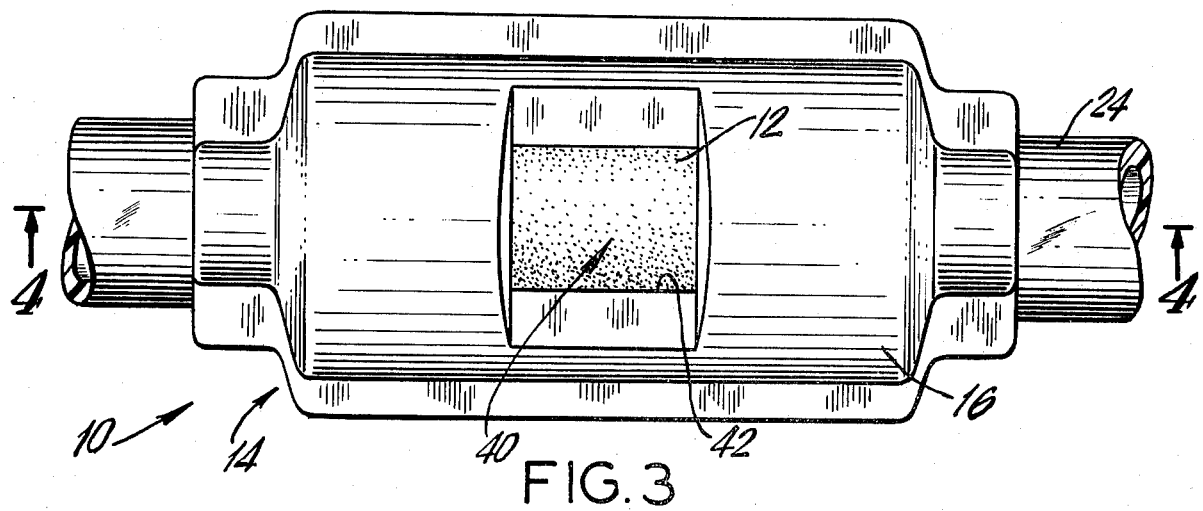
FIG. 3 is a top plan view of the resealable device of FIG. 1.

Referring to FIG. 2, the elastomeric tube 12 has a cylindrical inner recess 26 having a diameter (normal condition) approximately equal in size to the outer diameter of the tube 24 for mounting thereon and a predetermined outer diameter and length relative to a pair of cylindrically shaped half-cavities 28 and 30 formed in elements 16 and 18, respectively. For example, for a tube 24 having an outer diameter of 5/16 inch, the elastomeric tube 12 has an inner diameter of 5/16 inch, a sidewall thickness of ⅛ inch, and a length of ⅞ inch.

Figure 4:
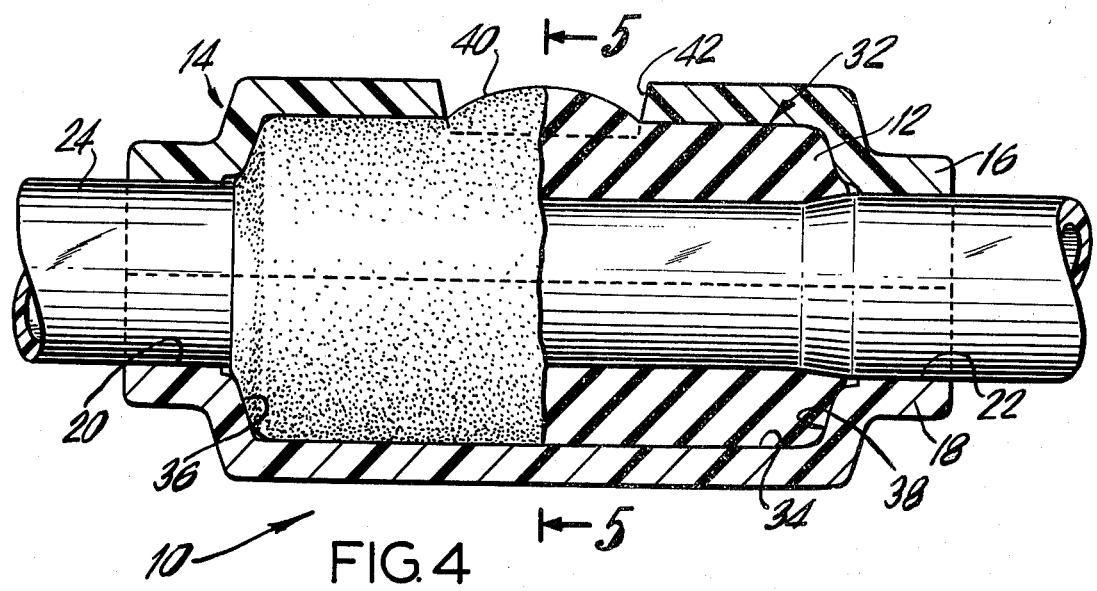
FIG. 4 is a partial cross-sectional view taken along line 4—4 of FIG. 3.
Figure 5:
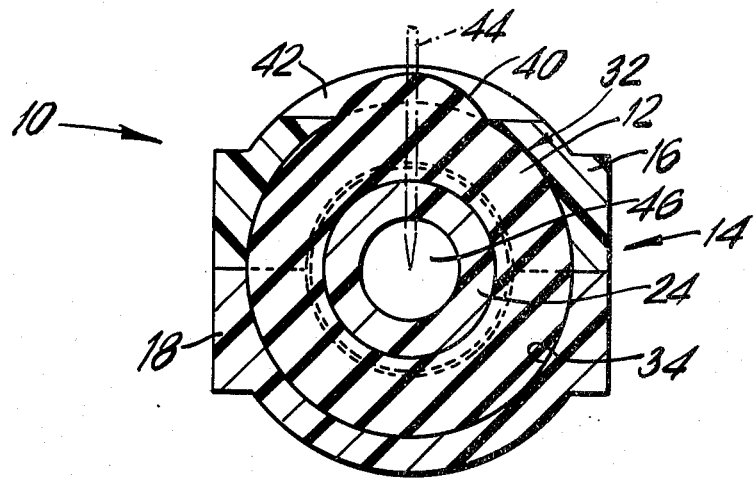
FIG. 5 is a cross-sectional view taken along line 5—5 of FIG. 3.

Upon fixedly joining of the half cavities 28 and 30 of the elements 16 and 18, a compression cavity 32 is created, see FIGS. 4 and 5. The compression cavity 32 has a diameter of approximately 9/16 inch, e.g., 1/32 inch less than the outer diameter of the elastomeric tube 12, and a length approximately ⅛ inch greater than the length of the elastomeric tube 12. Thus, upon assembly of the jacket 14 about the elastomeric tube the inner wall 34 of the compression cavity 32 engages and radially compresses the elastomeric tube 12 and also slightly compresses the tube 24. The radially compressed elastomeric tube 12 undergoes longitudinal expansion in the compression cavity 32 which is limited by fixed transverse stops 36 and 38. The fixed transverse stops 36 and 38 are formed at the ends of cavity 32 and are generally in the shape of truncated cones to direct and concentrate the compressive forces of the elastomeric tube 12 against the tube 24 to provide hermetic sealing therearound. Moreover, as a result of the radial compression of the elastomeric tube 12, a portion 40 bulges through the plane of a window 42 formed in the top element 16, thereby providing a crown or target for puncturing by a needle 44 (or cannula), see FIG. 5.

Referring to FIGS. 1 and 5, to insert a needle or cannula into the lumen 46 of the tube 24 for sampling the fluid, adding medication, or monitoring pressures, the person doing the puncturing grasps the device 10 firmly in one hand, preferably along the sides of the elements 16 and 18 where they are joined, usually applying an antiseptic solution, e.g., alcohol, to the window portion 40, and applies sufficient force to the needle 44 positioned at the crown 40 of the elastomeric tube 12 to puncture through the sidewall of the elastomeric tube 12 and into the lumen 46 of the fluid transmitting tube 24, thereby providing communication between the needle 44 and the lumen 46 of the tube 24 which enables sampling, monitoring, or injection into the lumen 46 as desired, see FIG. 5. During withdrawal of the needle 44, or cannula, the elastomeric tube 12 automatically contracts longitudinally and radially to hermetically reseal and effectively eliminate the needle opening in elastomeric tube 12 thereby preventing any leakage of fluid through the elastomeric tube 12 and additionally the elastomeric tube 12 effectively fills in the surface portion of the opening in the sidewall of the tube 24. The limited longitudinal expansion of the elastomeric tube 12 coacts with the radial compression obtained by jacket 14 to provide substantial homogeneous compression throughout the elastomeric member 12 and provides a hermetic seal between the tube 24 and the elastomeric member 12. This is accomplished by the fixed transverse stops or ends 36 and 38 of the cavity 32 which serve as rigid stops for limiting the longitudinal expansion of the elastomeric member 12, thereby concentrating and maintaining the elastic recoil energy of the elastomeric member 12 within the area defined by the cavity 32.

Advantageously, the jacket 14 is constructed of a material, such as a thermosetting or thermoplastic resinous material, e.g., styrene, which is substantially impenetrable to needles or cannulae in normal usage, so that if too much force is exerted on a needle or cannula it will not penetrate through the sidewall of jacket 18 and pierce the hand or fingers of the holder. Preferably, the window 42 of jacket 14 has its edges chamfered to eliminate pooling and facilitate drainage of the antiseptic solution applied to the window portion 40.

During experimental tests, a resealable device 10 in accordance with the present invention has withstood in excess of 50 needle punctures without leakage.

It should be understood by those skilled in the art that various modifications may be made in the present invention without departing from the spirit and scope thereof, as described in the description and defined in the appended claims.

What is claimed is:

1. A resealable device for repeated access to the lumen of a continuous walled conduit, comprising:
   a puncturable, elastomeric, generally tubular shaped member having a predetermined outer diameter and length, said tubular member being concentrically arranged about said conduit and in contact with said conduit; and
   rigid jacket means defining a cavity therein having a smaller diameter and longer length than said elastomeric member predetermined outer diameter and length, respectively, said jacket means being arranged concentrically about said conduit with said cavity about said elastomeric member, whereby said elastomeric member is radially compressed against said conduit, said jacket means defining an opening into said cavity to expose a portion of said elastomeric member for access by needles and cannulae and including fixed transverse stop means at each end of said cavity for limiting the longitudinal expansion of said elastomeric member to concentrate and maintain the elastic recoil energy of said elastomeric member against the conduit enabling said elastomeric member to reseal punctures therein and also provide a compression seal between said elastomeric member and the conduit, thereby preventing leakage from the conduit lumen after access thereto.

2. The resealable device recited in claim 1, wherein:
   said jacket means is formed of a material which is substantially impenetrable to needles and cannulae in normal usage.

3. The resealable device recited in claim 2, wherein:
   said jacket means has mating halves fixedly joined about said elastomeric member.

4. The resealable device recited in claim 1, wherein:
   said rigid stop means are generally in the shape of truncated cones.

5. The resealable device recited in claim 1, wherein:
   said exposed portion of said elastomeric member bulges out to form a target for needles and cannulae.

6. A resealable device for repeated access to the lumen of a continuous walled conduit, comprising:
   a puncturable, elastomeric, generally tubular shaped member having a predetermined outer diameter and length concentrically arranged about said conduit; and
   rigid jacket means defining a cavity therein having a smaller diameter and longer length than said elastomeric member predetermined outer diameter and length, respectively, said jacket means being arranged concentrically about said conduit with said cavity about said elastomeric member, whereby said elastomeric member is radially compressed, said jacket means defining an opening into said cavity to expose a portion of said elastomeric member for access by needles and cannulae and including fixed transverse stop means at each end of said cavity for limiting the longitudinal expansion of said elastomeric member to concentrate and maintain the elastic recoil energy of said elastomeric member against the conduit enabling said elastomeric member to reseal punctures therein and also provide a compression seal between said elastomeric member and the conduit, thereby preventing leakage from the conduit lumen after access thereto, and drainage means adjacent said opening for facilitating drainage of any liquid applied to the exposed portion of said elastomeric member prior to insertion of needles and cannulae therein.

* * * * *